US012194291B2

(12) United States Patent
Foster et al.

(10) Patent No.: US 12,194,291 B2
(45) Date of Patent: Jan. 14, 2025

(54) ELECTRICAL STIMULATION CUFF DEVICES AND SYSTEMS WITH HELICAL ARRANGEMENT OF ELECTRODES

(71) Applicant: Boston Scientific Neuromodulation Corporation, Valencia, CA (US)

(72) Inventors: Arthur J. Foster, Gary, SD (US); Pratap Arangil, Valencia, CA (US); Hari Hara Subramanian, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 350 days.

(21) Appl. No.: 17/747,471

(22) Filed: May 18, 2022

(65) Prior Publication Data

US 2022/0370793 A1 Nov. 24, 2022

Related U.S. Application Data

(60) Provisional application No. 63/191,449, filed on May 21, 2021.

(51) Int. Cl.
*A61N 1/05* (2006.01)
*A61N 1/36* (2006.01)

(52) U.S. Cl.
CPC ......... *A61N 1/0556* (2013.01); *A61N 1/0558* (2013.01); *A61N 1/3605* (2013.01)

(58) Field of Classification Search
CPC ... A61N 1/0556; A61N 1/0558; A61N 1/3605
See application file for complete search history.

(56) References Cited

U.S. PATENT DOCUMENTS 3,769,984 A 11/1973 Muench
3,941,136 A 3/1976 Bucalo
(Continued)

FOREIGN PATENT DOCUMENTS

EP 0234457 A2 9/1987
EP 0778047 A2 6/1997
(Continued)

OTHER PUBLICATIONS

Rattay, F., "Analysis of Models for External Stimulation of Axons," IEEE Transactions on Biomedical Engineering, BME-33(10): 974-977, 1986.
(Continued)

*Primary Examiner* — Eric D. Bertram
(74) *Attorney, Agent, or Firm* — Branch Partners PLLC; Bruce E. Black (57) ABSTRACT

An electrical stimulation lead includes a cuff having a cuff body having an exterior surface, an interior surface, and a circumference; longitudinally elongated electrodes disposed on the interior surface of the cuff body and helically arranged with each of the longitudinally elongated electrodes longitudinally offset relative to any adjacent longitudinally elongated electrodes; and a longitudinal slit extending through the cuff body and further extending along an entire length of the cuff body, the longitudinal slit operable to receive a portion of a target nerve from a region outside of the cuff to within the cuff body. The lead also includes a lead body coupled to the cuff and conductors extending through the lead body and the cuff with the conductors electrically coupled to the longitudinally elongated electrodes.

20 Claims, 8 Drawing Sheets

(56) References Cited

U.S. PATENT DOCUMENTS

| | | |
|---|---|---|
| 4,033,357 A | 7/1977 | Helland et al. |
| 4,135,518 A | 1/1979 | Dutcher |
| 4,257,428 A | 3/1981 | Barton et al. |
| 4,301,815 A | 11/1981 | Doring |
| 4,409,994 A | 10/1983 | Doring |
| 4,475,560 A | 10/1984 | Tarjan et al. |
| 4,506,679 A | 3/1985 | Mann |
| 4,542,753 A | 9/1985 | Brenman et al. |
| 4,573,481 A | 3/1986 | Bullara |
| 4,585,005 A | 4/1986 | Lue et al. |
| 4,628,944 A | 12/1986 | MacGregor et al. |
| 4,702,254 A | 10/1987 | Zabara |
| 4,716,888 A | 1/1988 | Wesner |
| 4,722,353 A | 2/1988 | Sluetz |
| 4,735,205 A | 4/1988 | Chachques et al. |
| 4,796,643 A | 1/1989 | Nakazawa et al. |
| 4,867,164 A | 9/1989 | Zabara |
| 4,920,979 A | 5/1990 | Bullara |
| 4,934,368 A | 6/1990 | Lynch |
| 4,957,118 A | 9/1990 | Erlebacher |
| 5,025,807 A | 6/1991 | Zabara |
| 5,095,905 A | 3/1992 | Klepinski |
| 5,139,539 A | 8/1992 | Haynes, Jr. |
| 5,143,067 A | 9/1992 | Rise et al. |
| 5,193,539 A | 3/1993 | Schulman et al. |
| 5,193,540 A | 3/1993 | Schulman et al. |
| 5,239,540 A | 8/1993 | Rovira et al. |
| 5,251,634 A | 10/1993 | Weinberg |
| 5,257,634 A | 11/1993 | Kroll |
| 5,282,468 A | 2/1994 | Klepinski |
| 5,312,439 A | 5/1994 | Loeb |
| 5,314,457 A | 5/1994 | Jeutter et al. |
| 5,324,322 A | 6/1994 | Grill et al. |
| 5,324,327 A | 6/1994 | Cohen |
| 5,376,108 A | 12/1994 | Collins et al. |
| 5,405,367 A | 4/1995 | Schulman et al. |
| 5,423,876 A | 6/1995 | Camps et al. |
| 5,433,735 A | 7/1995 | Zanakis et al. |
| 5,439,938 A | 8/1995 | Synder et al. |
| 5,454,840 A | 10/1995 | Krakovsky et al. |
| 5,480,420 A | 1/1996 | Hoegnelid et al. |
| 5,487,756 A | 1/1996 | Kallesoe et al. |
| 5,531,781 A | 7/1996 | Alferness et al. |
| 5,571,118 A | 11/1996 | Boutos |
| 5,741,319 A | 4/1998 | Woloszko et al. |
| 5,755,762 A | 5/1998 | Bush |
| 5,775,331 A | 7/1998 | Raymond et al. |
| 5,871,530 A | 2/1999 | Williams et al. |
| 5,876,399 A | 3/1999 | Chia et al. |
| 5,919,220 A | 7/1999 | Stieglitz et al. |
| 5,919,222 A | 7/1999 | Hjelle et al. |
| 5,922,015 A | 7/1999 | Schaldach et al. |
| 5,938,584 A | 8/1999 | Ardito et al. |
| 6,051,017 A | 4/2000 | Loeb et al. |
| 6,058,332 A | 5/2000 | Dahl |
| 6,061,596 A | 5/2000 | Richmond et al. |
| 6,151,526 A | 11/2000 | Tziviskos |
| 6,175,710 B1 | 1/2001 | Kamaji et al. |
| 6,175,764 B1 | 1/2001 | Loeb et al. |
| 6,181,965 B1 | 1/2001 | Loeb et al. |
| 6,181,969 B1 | 1/2001 | Fielding et al. |
| 6,181,973 B1 | 1/2001 | Ceron et al. |
| 6,185,452 B1 | 2/2001 | Schulman et al. |
| 6,185,455 B1 | 2/2001 | Loeb et al. |
| 6,188,932 B1 | 2/2001 | Lindegren |
| 6,201,994 B1 | 3/2001 | Warman et al. |
| 6,214,032 B1 | 4/2001 | Loeb et al. |
| 6,224,450 B1 | 5/2001 | Norton |
| 6,271,094 B1 | 8/2001 | Boyd et al. |
| 6,278,897 B1 | 8/2001 | Rutten et al. |
| 6,292,703 B1 | 9/2001 | Meier et al. |
| 6,295,944 B1 | 10/2001 | Lovett |
| 6,308,105 B1 | 10/2001 | Duysens et al. |
| 6,315,721 B2 | 11/2001 | Schulman et al. |
| 6,364,278 B1 | 4/2002 | Lin et al. |
| 6,391,985 B1 | 5/2002 | Goode et al. |
| 6,456,866 B1 | 9/2002 | Tyler et al. |
| 6,463,335 B1 | 10/2002 | Munch et al. |
| 6,516,227 B1 | 2/2003 | Meadows et al. |
| 6,582,441 B1 | 6/2003 | He et al. |
| 6,584,363 B2 | 6/2003 | Heil, Jr. et al. |
| 6,600,956 B2 | 7/2003 | Maschino et al. |
| 6,609,029 B1 | 8/2003 | Mann et al. |
| 6,609,032 B1 | 8/2003 | Woods et al. |
| 6,643,546 B2 | 11/2003 | Mathis et al. |
| 6,650,943 B1 | 11/2003 | Whitehurst et al. |
| 6,735,474 B1 | 5/2004 | Loeb et al. |
| 6,741,892 B1 | 5/2004 | Meadows et al. |
| 6,788,975 B1 | 9/2004 | Whitehurst et al. |
| 7,003,352 B1 | 2/2006 | Whitehurst |
| 7,006,875 B1 | 2/2006 | Kuzma et al. |
| 7,203,548 B2 | 4/2007 | Whitehurst et al. |
| 7,244,150 B1 | 7/2007 | Brase et al. |
| 7,248,930 B1 | 7/2007 | Woloszko et al. |
| 7,292,890 B2 | 11/2007 | Whitehurst et al. |
| 7,437,193 B2 | 10/2008 | Parramon et al. |
| 7,450,997 B1 | 11/2008 | Pianca et al. |
| 7,460,913 B2 | 12/2008 | Kuzma et al. |
| 7,584,004 B2 | 9/2009 | Caparso et al. |
| 7,596,414 B2 | 9/2009 | Whitehurst et al. |
| 7,610,103 B2 | 10/2009 | Whitehurst et al. |
| 7,672,734 B2 | 3/2010 | Anderson et al. |
| 7,706,892 B2 | 4/2010 | Colvin et al. |
| 7,761,165 B1 | 7/2010 | He et al. |
| 7,783,359 B2 | 8/2010 | Meadows |
| 7,783,362 B2 | 8/2010 | Whitehurst et al. |
| 7,792,590 B1 | 9/2010 | Pianca et al. |
| 7,809,446 B2 | 10/2010 | Meadows |
| 7,840,279 B2 | 11/2010 | He |
| 7,949,395 B2 | 5/2011 | Kuzma |
| 7,953,498 B1 | 5/2011 | Carbunaru et al. |
| 7,974,706 B2 | 7/2011 | Moffitt et al. |
| 7,996,092 B2 | 8/2011 | Mrva et al. |
| 8,019,443 B2 | 9/2011 | Schleicher et al. |
| 8,155,757 B1 | 4/2012 | Neisz et al. |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,364,278 B2 | 1/2013 | Pianca et al. |
| 8,391,985 B2 | 3/2013 | McDonald |
| 8,423,154 B2 | 4/2013 | Malinowski et al. |
| 8,423,157 B2 | 4/2013 | Moffitt et al. |
| 8,483,237 B2 | 7/2013 | Zimmermann et al. |
| 8,594,805 B2 | 11/2013 | Hincapie Ordonez et al. |
| 8,606,362 B2 | 12/2013 | He et al. |
| 8,612,025 B2 | 12/2013 | Neisz et al. |
| 8,620,436 B2 | 12/2013 | Parramon et al. |
| 8,688,235 B1 | 4/2014 | Pianca et al. |
| 8,718,790 B2 | 5/2014 | Pianca |
| 8,768,488 B2 | 7/2014 | Barker |
| 8,818,524 B2 | 8/2014 | Hincapie Ordonez et al. |
| 8,831,742 B2 | 9/2014 | Pianca et al. |
| 8,849,422 B2 | 9/2014 | Pianca |
| 8,934,992 B2 | 1/2015 | Johnson et al. |
| 9,308,383 B2 | 4/2016 | Didon |
| 9,568,053 B2 | 2/2017 | Tebay |
| 9,586,053 B2 | 3/2017 | Moffitt et al. |
| 9,907,950 B1 | 3/2018 | Perryman et al. |
| 10,350,413 B2 | 7/2019 | Moffitt et al. |
| 10,485,969 B2 | 11/2019 | Govea et al. |
| 10,493,269 B2 | 12/2019 | Stoffregen et al. |
| 10,537,741 B2 | 1/2020 | Bradley et al. |
| 10,709,888 B2 | 7/2020 | Pianca |
| 10,814,127 B2 | 10/2020 | Nageri et al. |
| 2002/0022873 A1 | 2/2002 | Erickson et al. |
| 2003/0040785 A1 | 2/2003 | Maschino et al. |
| 2003/0045919 A1 | 3/2003 | Swoyer et al. |
| 2003/0074039 A1 | 4/2003 | Puskas |
| 2003/0078623 A1 | 4/2003 | Weinberg et al. |
| 2003/0114905 A1 | 6/2003 | Kuzma |
| 2003/0199938 A1 | 10/2003 | Smits et al. |
| 2003/0236558 A1 | 12/2003 | Whitehurst et al. |
| 2004/0010303 A1 | 1/2004 | Bolea et al. |

(56) References Cited

U.S. PATENT DOCUMENTS

| | | |
|---|---|---|
| 2004/0034401 A1 | 2/2004 | Dahlberg et al. |
| 2004/0049240 A1 | 3/2004 | Gerber et al. |
| 2004/0059392 A1 | 3/2004 | Parramon et al. |
| 2004/0111139 A1 | 6/2004 | McCreery |
| 2004/0230280 A1 | 11/2004 | Cates et al. |
| 2005/0010265 A1 | 1/2005 | Baru Fassio et al. |
| 2005/0065589 A1 | 3/2005 | Schneider et al. |
| 2005/0177220 A1 | 8/2005 | Iaizzo et al. |
| 2005/0182472 A1 | 8/2005 | Wahlstrom et al. |
| 2006/0161204 A1 | 7/2006 | Colvin et al. |
| 2006/0173522 A1 | 8/2006 | Osorio |
| 2006/0184204 A1 | 8/2006 | He |
| 2006/0212075 A1 | 9/2006 | Marnfeldt |
| 2006/0241737 A1 | 10/2006 | Tockman et al. |
| 2006/0282145 A1 | 12/2006 | Caparso et al. |
| 2007/0150036 A1 | 6/2007 | Anderson |
| 2007/0179559 A1* | 8/2007 | Giftakis ............. A61N 1/36007 607/46 |
| 2007/0219595 A1 | 9/2007 | He |
| 2008/0046055 A1 | 2/2008 | Durand et al. |
| 2008/0071320 A1 | 3/2008 | Brase |
| 2008/0103545 A1 | 5/2008 | Bolea et al. |
| 2009/0043352 A1 | 2/2009 | Brooke et al. |
| 2009/0118727 A1 | 5/2009 | Pearson et al. |
| 2009/0187222 A1 | 7/2009 | Barker |
| 2009/0210042 A1 | 8/2009 | Kowalczewski |
| 2009/0275956 A1 | 11/2009 | Burnes et al. |
| 2009/0276021 A1 | 11/2009 | Meadows et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2010/0049276 A1 | 2/2010 | Blum et al. |
| 2010/0076535 A1 | 3/2010 | Pianca et al. |
| 2010/0114202 A1 | 5/2010 | Donofrio et al. |
| 2010/0121405 A1* | 5/2010 | Ternes ................. A61N 1/0556 607/37 |
| 2010/0168831 A1 | 7/2010 | Korivi et al. |
| 2010/0241207 A1 | 9/2010 | Bluger |
| 2010/0268298 A1 | 10/2010 | Moffitt et al. |
| 2010/0298916 A1 | 11/2010 | Rabischong et al. |
| 2010/0312320 A1 | 12/2010 | Faltys et al. |
| 2011/0004267 A1 | 1/2011 | Meadows et al. |
| 2011/0005069 A1 | 1/2011 | Pianca |
| 2011/0078900 A1 | 4/2011 | Pianca et al. |
| 2011/0130803 A1 | 6/2011 | McDonald |
| 2011/0130817 A1 | 6/2011 | Chen |
| 2011/0130818 A1 | 6/2011 | Chen |
| 2011/0160810 A1 | 6/2011 | Griffith |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0071949 A1 | 3/2012 | Pianca et al. |
| 2012/0078320 A1 | 3/2012 | Schotzko et al. |
| 2012/0165898 A1 | 6/2012 | Moffitt |
| 2012/0165911 A1 | 6/2012 | Pianca |
| 2012/0185027 A1 | 7/2012 | Pianca et al. |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0277819 A1 | 11/2012 | Cowley et al. |
| 2012/0316615 A1 | 12/2012 | Digiore et al. |
| 2013/0023974 A1 | 1/2013 | Amrani |
| 2013/0105071 A1 | 5/2013 | Digiore et al. |
| 2013/0172973 A1 | 7/2013 | Tockman et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317518 A1 | 11/2013 | Govea |
| 2013/0317587 A1 | 11/2013 | Barker |
| 2013/0325091 A1 | 12/2013 | Pianca et al. |
| 2013/0338733 A1 | 12/2013 | Goddard et al. |
| 2014/0039587 A1 | 2/2014 | Romero |
| 2014/0046407 A1 | 2/2014 | Ben-Ezra et al. |
| 2014/0074213 A1 | 3/2014 | Neisz et al. |
| 2014/0094887 A1 | 4/2014 | True et al. |
| 2014/0094888 A1 | 4/2014 | True et al. |
| 2014/0128950 A1 | 5/2014 | Thota et al. |
| 2014/0188202 A1 | 7/2014 | Zarembo et al. |
| 2014/0228905 A1 | 8/2014 | Bolea |
| 2014/0277284 A1 | 9/2014 | Chen et al. |
| 2014/0353001 A1 | 12/2014 | Romero et al. |
| 2014/0358207 A1 | 12/2014 | Romero |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0119965 A1 | 4/2015 | Govea |
| 2015/0151113 A1 | 6/2015 | Govea et al. |
| 2015/0174396 A1 | 6/2015 | Fisher et al. |
| 2015/0202433 A1 | 7/2015 | Franke et al. |
| 2015/0202446 A1 | 7/2015 | Franke et al. |
| 2015/0366467 A1 | 12/2015 | De Kock et al. |
| 2016/0136443 A1 | 5/2016 | Grandhe et al. |
| 2017/0224982 A1 | 8/2017 | Nageri et al. |
| 2017/0239462 A1* | 8/2017 | Govea ................. A61N 1/0556 |
| 2017/0333692 A1 | 11/2017 | Stoffregen et al. |
| 2017/0348522 A1 | 12/2017 | Stoffregen et al. |
| 2018/0028804 A1 | 2/2018 | Pianca |
| 2018/0071520 A1 | 3/2018 | Weerakoon et al. |
| 2018/0154156 A1 | 6/2018 | Clark et al. |
| 2018/0318578 A1 | 11/2018 | Ng et al. |
| 2019/0083796 A1 | 3/2019 | Weerakoon et al. |
| 2020/0113477 A1* | 4/2020 | Dowrick ............. A61B 5/0538 |
| 2020/0230421 A1* | 7/2020 | Zaidi ..................... A61N 1/372 |
| 2020/0316372 A1 | 10/2020 | Bashirullah et al. |
| 2020/0384265 A1 | 12/2020 | Donega et al. |
| 2022/0226641 A1 | 7/2022 | Subramanian |

FOREIGN PATENT DOCUMENTS

| | | |
|---|---|---|
| WO | 98/37926 | 9/1998 |
| WO | 98/43700 | 10/1998 |
| WO | 98/43701 | 10/1998 |
| WO | 2008019483 | 2/2008 |
| WO | 2008048471 | 4/2008 |
| WO | 2013188871 | 12/2013 |
| WO | 2020/051484 | 3/2020 |

OTHER PUBLICATIONS

Plachta et al., "Blood pressure control with selective vagal nerve stimulation and minimal side effects," J. Neural Eng. 11 (2014) 036011 (15pp), 2014.

Polasek et al., "Stimulation Stability and Selectivity of Chronically Implanted Multicontact Nerve Cuff Electrodes In the Human Upper Extremity," IEEE Transactions on Neural Systems and Rehabilitation Engineering, vol. 17, No. 5, 428-437, Oct. 2009.

Rozman et al., "Selective Stimulation of Autonomic Nerves and Recording of Electroneurograms in a Canine Model," Artificial Organs, 21(8): 592-596, 2008.

International Search Report and Written Opinion for PCT Application No. PCT/US22/29816 mailed Oct. 20, 2020.

Invitation to Pay Additional Fees for PCT Application No. PCT/US22/29816 mailed Aug. 29, 2022.

* cited by examiner

ELECTRICAL STIMULATION CUFF DEVICES AND SYSTEMS WITH HELICAL ARRANGEMENT OF ELECTRODES

CROSS-REFERENCE TO RELATED APPLICATIONS

This application claims the benefit under 35 U.S.C. § 119(e) of U.S. Provisional Patent Application Ser. No. 63/191,449, filed May 21, 2021, which is incorporated herein by reference.

FIELD

The present disclosure is directed to the area of implantable electrical stimulation systems and methods of making and using the systems. The present disclosure is also directed to implantable electrical stimulation cuff devices, as well as methods of making and using the same.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One aspect is an electrical stimulation lead that includes a cuff having a cuff body having an exterior surface, an interior surface, and a circumference; a plurality of longitudinally elongated electrodes disposed on the interior surface of the cuff body and helically arranged with each of the longitudinally elongated electrodes longitudinally offset relative to any adjacent longitudinally elongated electrodes; and a longitudinal slit extending through the cuff body and further extending along an entire length of the cuff body, the longitudinal slit operable to receive a portion of a target nerve from a region outside of the cuff to within the cuff body. The lead also includes a lead body coupled to the cuff and a plurality of conductors extending through the lead body and the cuff with the conductors electrically coupled to the longitudinally elongated electrodes.

In at least some aspects, each of the longitudinally elongated electrodes has a width of no more than 100 μm. In at least some aspects, each of the longitudinally elongated electrodes has a length of at least 0.5 mm. In at least some aspects, the longitudinally elongated electrodes are arranged in at least one helical turn.

In at least some aspects, the longitudinally elongated electrodes are arranged in at least two helical turns. In at least some aspects, each of the helical turns includes at least eight of the longitudinally elongated electrodes. In at least some aspects, the longitudinally elongated electrodes of each of the helical turns are longitudinally aligned with corresponding ones of the longitudinally elongated electrodes of each of the other helical turns. In at least some aspects, the longitudinally elongated electrodes of at least one of the helical turns are circumferentially staggered relative to corresponding ones of the longitudinally elongated electrodes of at least one of the other helical turns.

In at least some aspects, the plurality of longitudinally elongated electrodes includes at least 20 of the longitudinally elongated electrodes. In at least some aspects, each of the longitudinally elongated electrodes is longitudinally offset from each adjacent one of the longitudinally elongated electrodes by at least 0.2 mm. In at least some aspects, each of the longitudinally elongated electrodes is longitudinally offset from each adjacent one of the longitudinally elongated electrodes by at least 10 percent of a length of the longitudinally elongated electrodes.

In at least some aspects, the cuff further includes at least one radial electrode extending around at least 10% of the circumference of the cuff body. In at least some aspects, the at least one radial electrodes extends around at least 75% of the circumference of the cuff body. In at least some aspects, at least one of the at least one radial electrodes is disposed on the cuff body is disposed at an end of the helical arrangement of the longitudinally elongated electrodes. In at least some aspects, the at least one radial electrodes includes two radial electrodes disposed at opposite ends of the helical arrangement of the longitudinally elongated electrodes. In at least some aspects, at least one of the at least one radial electrodes is disposed radially opposite of at least one of the longitudinally elongated electrodes.

In at least some aspects, the electrical stimulation lead further includes a cushioning layer disposed over the interior surface of the cuff body. In at least some aspects, the cuff body has a length of at least 10 mm. In at least some aspects, the electrical stimulation lead further includes a plurality of terminals disposed along the lead body and electrically coupled to the longitudinally elongated electrodes by the conductors.

A further aspect is an electrical stimulation lead that includes a cuff having a helical cuff body having an exterior surface and an interior surface and defining at least one helical turn, and electrodes disposed on the interior surface of the helical cuff body, wherein each of the at least one helical turn include at least eight of the electrodes. The electrical stimulation lead also includes a lead body coupled to the cuff and conductors extending through the lead body and the cuff with the conductors electrically coupled to the electrodes.

In at least some aspects, the helical cuff body defines at least two helical turns. In at least some aspects, each of the helical turns of the helical cuff body has a pitch of at least 1 mm. In at least some aspects, adjacent pairs of the electrodes are separated by at least 0.02 mm. In at least some aspects, each of the electrodes has a length or width of at least 0.1 mm.

Another aspect is an electrical stimulation system that includes any of the electrical stimulation described above and a control module configured to receive a portion of the lead body of the electrical stimulation lead and to electrically couple to the longitudinally elongated electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation cuff devices, as well as methods of making and using the same.

Suitable implantable electrical stimulation systems include, but are not limited to, a least one lead with one or more electrodes disposed along a distal end of the lead.

Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,203,548; 7,244,150; 7,450,997; 7,596,414; 7,610,103; 7,672,734; 7,761,165; 7,783,359; 7,792,590; 7,809,446; 7,949,395; 7,974,706; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference in their entireties.

Figure 1:
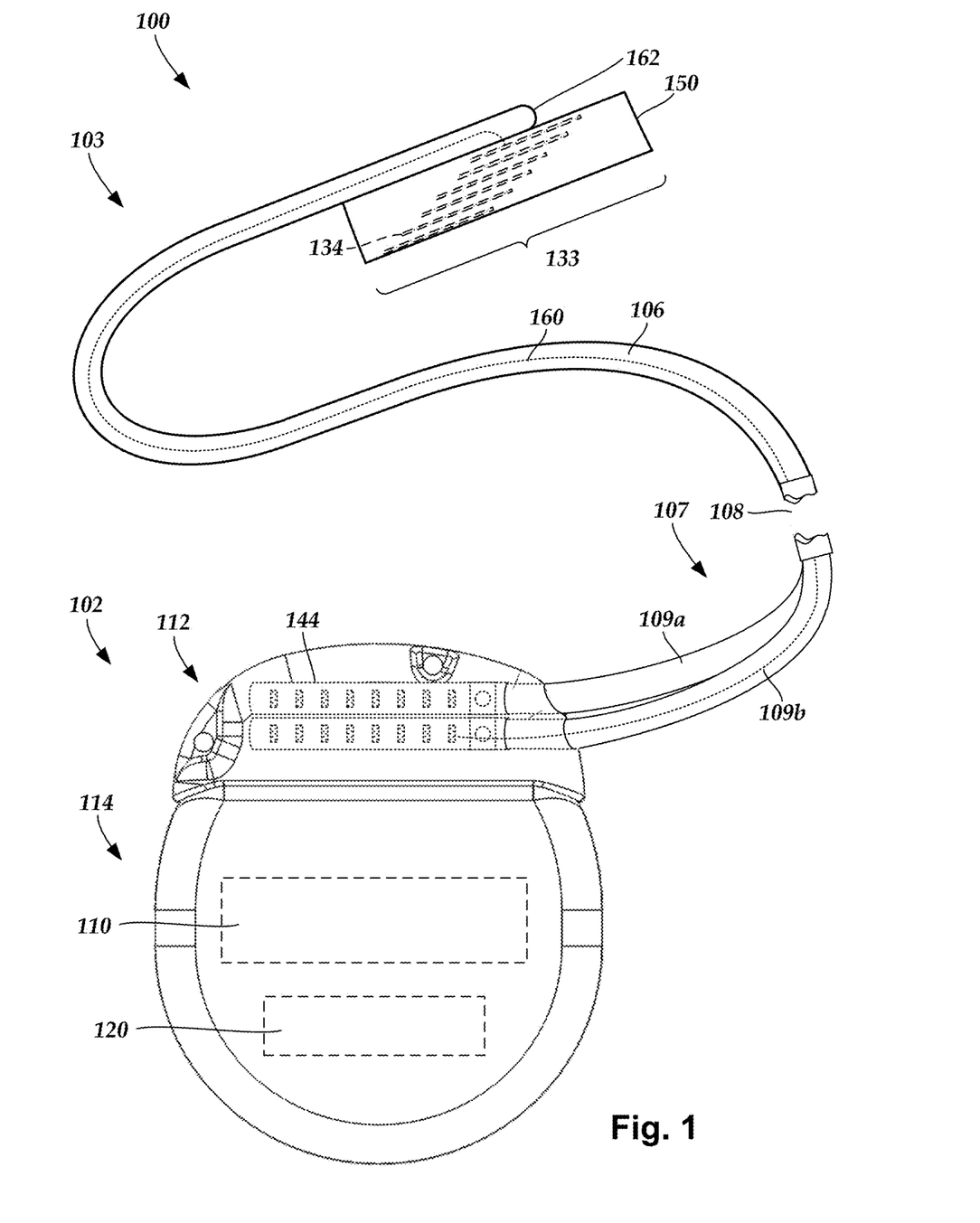
FIG. 1 is a schematic view of one embodiment of an electrical stimulation system that includes a lead electrically coupled to a control module.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a mount 162 and a cuff 150. The lead 103 includes one or more lead bodies 106, an array of electrodes 133, such as electrode 134, and an array of terminals (e.g., 210 in FIG. 2A-2B) disposed within the cuff 150 attached to the one or more lead bodies 106. In at least some embodiments, the lead is isodiametric along at least a portion of the longitudinal length of the lead body 106. FIG. 1 illustrates one lead 103 coupled to a control module 102. Other embodiments may include two, three, four, or more leads 103 coupled to the control module 102. In yet other embodiments, a lead 103 may be coupled to multiple control modules 102. For example, a lead with 64 electrodes may be coupled to two control modules 102 that are capable of handling 32 electrodes each.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 1, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more proximal tails 109a and 109b configured and arranged to couple to the control module 102 (or another splitter, a lead extension, an adaptor, or the like). The splitter 107 and splitter connector 108 may be part of the lead 103 or may be a separate component that attaches to the lead.

The control module 102 typically includes a connector housing 112 and a sealed electronics housing 114. Stimulation circuitry 110 and an optional power source 120 are disposed in the electronics housing 114. A control module connector 144 is disposed in the connector housing 112. The control module connector 144 is configured and arranged to make an electrical connection between the lead 103 and the stimulation circuitry 110 of the control module 102.

The electrical stimulation system or components of the electrical stimulation system, including the lead body 106 and the control module 102, are typically implanted into the body of a patient. The electrical stimulation system can be used for a variety of applications including, but not limited to, brain stimulation, neural stimulation, spinal cord stimulation, muscle stimulation, and the like.

The lead body 106 can be made of, for example, a non-conductive, biocompatible material such as, for example, silicone, polyurethane, polyetheretherketone ("PEEK"), epoxy, and the like or combinations thereof. The lead body 106 may be formed in the desired shape by any process including, for example, molding (including injection molding), casting, and the like. The non-conductive material typically extends from the distal end of the lead body 106 to the proximal end of the lead body 106.

Figure 2A:
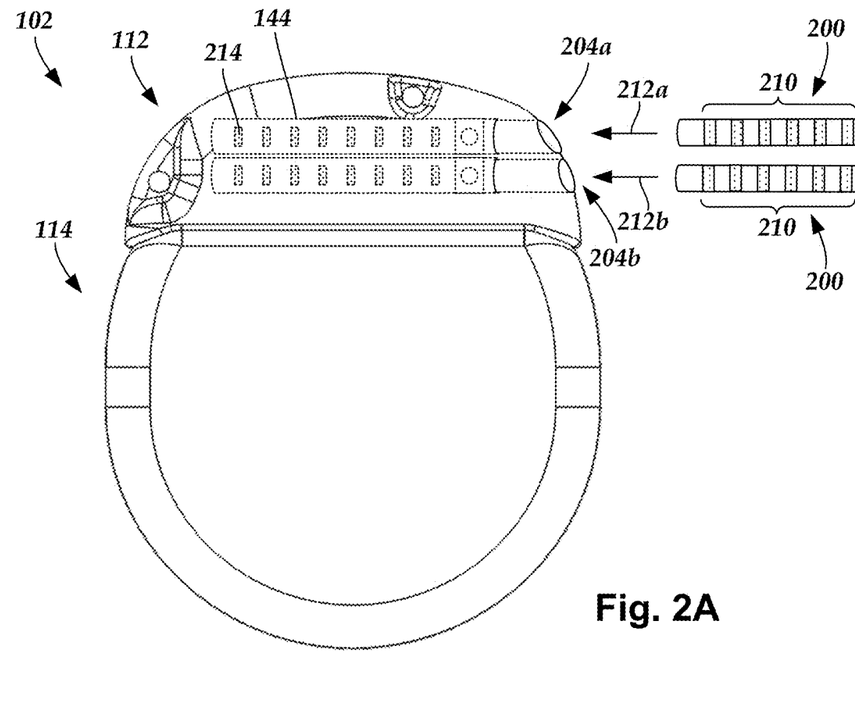
FIG. 2A is a schematic view of one embodiment of the control module of FIG. 1 configured and arranged to electrically couple to an elongated device.
Figure 2B:
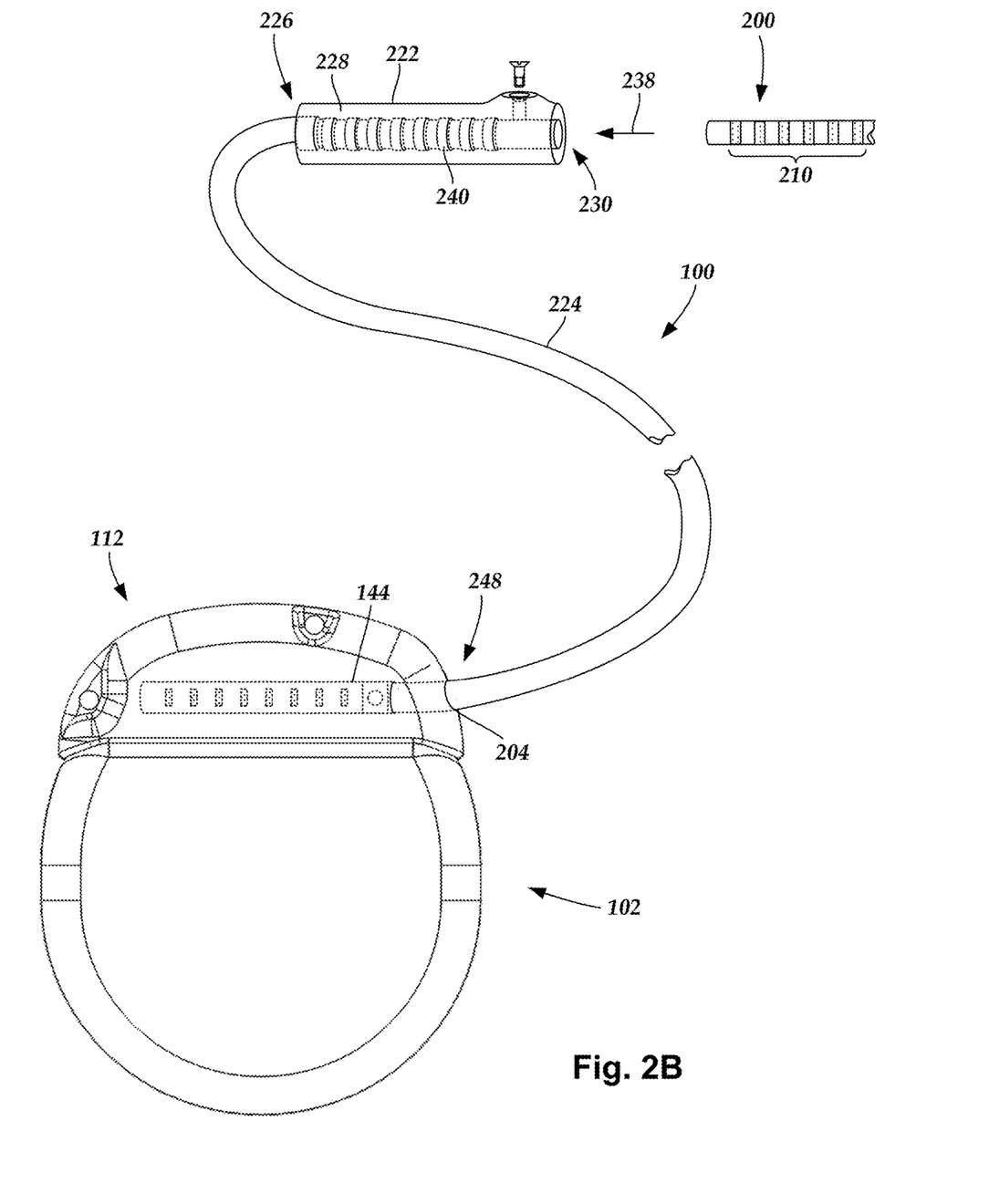
FIG. 2B is a schematic view of one embodiment of a lead extension configured and arranged to electrically couple the elongated device of FIG. 2A to the control module of FIG. 1.

Terminals (e.g., 210 in FIGS. 2A-2B) are typically disposed along the proximal end of the lead body 106 of the electrical stimulation system 100 (as well as any splitters, lead extensions, adaptors, or the like) for electrical connection to corresponding connector contacts (e.g., 214 and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires 160, cables, or the like (only one of which is shown in FIG. 1) extend from the terminals to the electrodes 134. Typically, one or more electrodes 134 are electrically coupled to each terminal. In at least some embodiments, each terminal is only connected to one electrode 134.

The electrically conductive wires ("conductors") 160 (only one of which is illustrated in FIG. 1 for clarity) may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the lead body 106. In at least one embodiment, the one or more lumens are flushed continually, or on a regular basis, with saline, epidural fluid, or the like. In at least some embodiments, the one or more lumens are permanently or removably sealable at the distal end.

FIG. 1 also illustrates a mount 162, part of the lead body 106, coupled to cuff 150. The conductors 160 (only one of which is illustrated in FIG. 1 for clarity) from within the lead body 106 are received in the mount 162, which in turn is attached to the cuff 150 such that each conductor passes through the mount 162 for a direct electrical connection with one of the electrodes 134 (e.g., one conductor is electrically connected with one electrode and so on). The mount 162 may be attached using a variety of means such as, but not limited to, molding or adhering the mount 162 to the cuff 150. In other embodiments, the conductors 160 from within the lead body 106 are electrically coupled to the electrodes 134 using jumper, intermediate or transition wires from the lead body 106 to the electrodes 134.

The mount 162 can be offset from the cuff 150, as illustrated in FIG. 1, or in-line with the cuff or in any other suitable arrangement. Examples of cuff leads 103 can be found at U.S. Pat. Nos. 7,596,414; 7,974,706; 8,423,157; 10,485,969; 10,493,269; 10,709,888; and 10,814,127; and U.S. Patent Application Publications Nos. 2017/0333692 and 2018/0154156, all of which are incorporated herein by reference in their entireties.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the lead extension 224 of FIG. 2B, an adaptor, or the like or combinations thereof), or a combination thereof. FIG. 2A illustrates two elongated devices 200 coupled to the control module 102. These two elongated devices 200 can be two tails as illustrated in FIG. 1 or two different leads or any other combination of elongated devices.

The control module connector 144 defines at least one port into which a proximal end of the elongated device 200 can be inserted, as shown by directional arrow 212. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference in their entireties.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Conventional cuff leads include a cuff that wraps around a portion of a nerve with one or more electrodes arranged on the cuff. In many conventional cuff leads, the individual electrodes also wrap around at least a portion of the circumference of a nerve in a radial wrap arrangement. The radial wrap arrangement of the electrodes typically results in stimulation of a circumferential region of the nerve.

In contrast to conventional cuff leads with radial electrodes, cuff leads can include longitudinally elongated electrodes in a helical arrangement for stimulation of nerves. In at least some embodiments, the cuffs can be useful to provide differential internal organ stimulation or control by stimulating nerves leading to those organs. Differential organ control can be useful for providing therapy for disorders of, for example, the cardio-vascular system, the pulmonary system, the gastrointestinal system, the urinary system, and other internal organ systems.

In at least some embodiments, a nerve cuff with a helical arrangement of elongated electrodes can produce diameter-selective stimulation of the vagus or other nerves. In at least some instances, diameter-selective vagus nerve stimulation can be used for differential control of specific internal organs. In at least some embodiments, positioning the elongated electrodes in a helical arrangement can facilitate sensing of nerve impulses. In at least some embodiments, as compared to conventional stimulation cuffs, positioning the electrodes in a helical arrangement can provide a larger surface area from an electrical diagonal slice of the nerve between two selected electrodes for stimulation. In at least some embodiments, the cuff lead can be used to block nerve impulses to or from an organ or other body structure.

A cuff lead can include a cuff body that wraps around a nerve and further include longitudinally elongated electrodes in a helical arrangement on the interior surface of the cuff body. The helical arrangement can include any suitable number of full or partial helical turns helical turns including, but not limited to, 0.5, 1, 1.25, 1.5, 1.75, 2, 2.5, 3, 4, 5, 6, 7, 8, 9, 10, or more helical turns. In at least some embodiments, there are at least 8, 9, 10, 11, 12, 16, 20, 25, 28, 32, 36, 40, 48, 50, 64, 80, 99, 100, 120, 128, 150, 200, 250, 256, or more elongated electrodes in each helical turn with partial helical turns including a corresponding fraction of the number of elongated electrodes.

In at least some embodiments, the cuff may also include one or more radial electrodes that can be used as a counter-electrode to one or more selected elongated electrodes. In at least some embodiments, a radial electrode extends around at least 10, 20, 25, 30, 33, 40, 50, 60, 75, 80, 90, or 95 percent of a circumference of the cuff body. In at least some embodiments, a radial electrode can be disposed at one or both ends of the helical arrangement of elongated electrodes. In at least some embodiments, one or more radial electrodes can be positioned radially opposite one or more of the elongated electrodes. In at least some embodiments, one or more of the elongated electrodes can be used as a cathode(s) and one or more of the radial electrodes can be used as an anode(s). Any other suitable selection of cathode(s) or anode(s) from the elongated or radial electrodes can be used.

Figure 3:
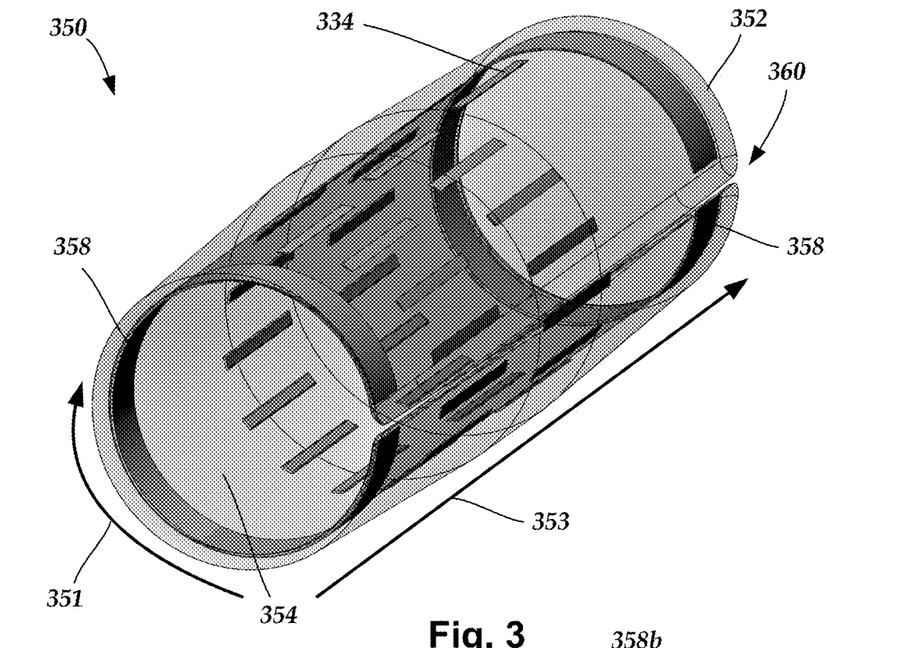
FIG. 3 is a schematic perspective view of one embodiment of a cuff with 28 helically-arranged elongated electrodes and two radial electrodes.

FIG. 3 illustrates one embodiment of a cuff 350 of a cuff lead 103 (FIG. 1). The cuff 350 includes a cuff body 352 with longitudinally elongated electrodes 334 disposed on an interior surface 354 of the cuff body and arranged around the circumference of the cuff body in a helical arrangement. In the illustrated embodiment, the helical arrangement includes 28 elongated electrodes 334 arranged in two helical turns. Any other suitable number of electrodes can be used including, but not limited to, 8, 9, 10, 11, 12, 16, 20, 25, 28, 32, 36, 40, 48, 50, 64, 80, 99, 100, 120, 128, 150, 200, 250, 256, or more elongated electrodes in each helical turn. The number of elongated electrodes 334 can be the same for each helical turn or can differ between helical turns. In at least some embodiments, the elongated electrodes 334 can be arranged in a double or triple helix.

For arrangements with more than one helical turn, corresponding elongated electrodes 334 of each helical turn (e.g., the first elongated electrodes of helical turn) can be longitudinally aligned (e.g., aligned along a single longitudinal line parallel to the longitudinal axis of the cuff 350) with each other or can be circumferentially staggered with respect to each other (e.g., not aligned along a single longitudinal line parallel to the longitudinal axis of the cuff 350).

In the illustrated embodiment, the elongated electrodes 334 of each helical turn are uniformly spaced around the circumference 351 of the cuff body. In other embodiments, the elongated electrodes 334 of each helical turn can be non-uniformly spaced around the circumference 351 of the cuff body.

In at least some embodiments, the pitch of the helical turns is no more then 1, 2, 3, 4, 5, 6, 7, 8, 9, or 10 mm. For arrangements with more than one helical turn, the helical turns can have the same or different pitches.

In addition, the cuff 350 includes a radial electrodes 358 that wraps around at least 20, 25, 30, 33, 40, 50, 60, 75, 80, 90, or 95 percent of the circumference of the cuff body 352. In the illustrated embodiment, a radial electrode 358 is disposed at both ends of the helical arrangement of elongated electrodes 334.

The cuff 350 also defines a slit 360 that extends the longitudinal length of the cuff body 352 so that the nerve can be loaded into the interior 362 of the cuff body by opening the slit to fit the cuff body over the nerve. The slit 360 is opened or initially sized to allow the target nerve (not shown) to be slipped, inserted, fed, or otherwise received into the cuff 350 such that the cuff 350 wraps around the target nerve. In at least some embodiments, the slit 360 allows the cuff 350 to be easily moved over and around the target nerve or relative to the target nerve whether rotationally or transitionally. In at least some embodiments, the slit 360 is self-sealing when the cuff 350 is positioned around the nerve.

The electrodes 334, 358 can be formed using any conductive, biocompatible material. Examples of suitable materials include metals, alloys, conductive polymers, conductive carbon, and the like, as well as combinations thereof. In at least some embodiments, one or more of the electrodes 334 are formed from one or more of: platinum, platinum alloys such as platinum iridium, palladium alloys such as palladium rhodium, titanium, titanium alloys, nickel alloys, cobalt alloys, nickel/cobalt alloys, stainless steels, tantalum, conductive carbon, conductive plastics, epoxy, or other adhesive filled with metallic powder, Nitinol™, or the like or any combination thereof. The electrodes 334, 358 can be formed by any suitable process including, but not limited to, machining, molding (for example, powdered metal molding), photolithography, additive techniques, stamping, or the like or any combination thereof.

In at least some embodiments, the electrodes 334, 358 have a contact surface that is flush or slightly protruding (for example, no more than 200, 100, or 50 μm) from the cuff body 352 which, at least in some circumstances, may reduce or eliminate physical pressure on the nerve. It will be recognized that the electrodes can be used to provide electrical stimulation or to sense electrical signals from tissue or any combination thereof.

In at least some embodiments, the elongated electrodes 334 have a width of no more than 250, 200, 150, 100, 75, 50, 40, 30, or 25 micrometers (μm) and a length of at least 0.5, 1, 1.5, 2, 2.5, 3, 4, 5, 7, or more millimeters (mm). The width of the elongated electrodes corresponds to a distance in the circumferential direction 351 around the cuff body. In at least some embodiments, the length of the elongated electrodes 334 is no more than 10 mm. The length of the elongated electrodes corresponds to a distance along the longitudinal direction 353 of the cuff body. In at least some embodiments, the elongated electrodes 334 have an aspect ratio (length/width) or at least 5, 10, 20, 40, 50, 80, 100, 150, 200, or more. In at least some embodiments, each of the elongated electrodes 334 has the same width, length, and aspect ratio. In other embodiments, the elongated electrodes 334 can have different widths, lengths, or aspect ratios.

In the illustrated embodiment, each of the elongated electrodes 334 is longitudinally offset from the immediately adjacent elongated electrodes by a uniform amount. In other embodiments, the longitudinal offset between immediately adjacent elongated electrodes can be vary along the cuff 350. In at least some embodiments, the longitudinal offset between immediately adjacent elongated electrodes 334 is at least 0.2, 0.25, 0.3, 0.5, 0.75, 1, or 1.5 mm or more or is at least 10, 20, 25, 30, 33, 40, or 50 percent or more of the length of the elongated electrodes. In at least some embodiments, the longitudinal offset between immediately adjacent elongated electrodes 334 is no more than 3, 2.5, 2, 1.5, 1, or 0.5 mm or less or no more than 90, 80, 75, 66, 50, 40, 33, 30, 25, 20, or 10 percent or less of the length of the elongated electrodes.

In at least some embodiments, the elongated electrodes 334 and radial electrodes 358 are rectangular or rectangular with rounded corners. Any other suitable shape can be used for the elongated electrodes including, but not limited to, oblong, oval, modified rectangular with one or more sides (or portions of sides) that are curved, or the like or any combination thereof. The length and width measurements described above correspond to the longest or widest portion of the elongated electrode 334 or radial electrode 358. For example, for an oval electrode, the length along the major axis of the oval corresponds to the length measurement and the length along the minor axis corresponds to the width measurement.

Stimulation can be performed using one or more of the elongated electrodes 334. One or more of the radial electrode 358 (or one or more of the elongated electrodes 334) can be selected as the counter-electrode.

The cuff body 352 can be formed of any suitable biocompatible and biostable non-conductive material including, but not limited to, polymer materials such as silicone, polyurethane, polyetheretherketone ("PEEK"), epoxy, or the like or any combination thereof. In at least some embodiments, the cuff body 352 can have a circular, oval, or any other suitable cross-sectional shape and, at least in some embodiments, may be sufficiently flexible to alter the cross-sectional shape to accommodate the nerve. In at least some embodiments, the electrodes 334, 358 can be molded with the cuff body 352 or formed by techniques such as etching or ablation of conductive layers, films, or the like. In at least some embodiments, the cuff body 352 has an inner diameter (which can correspond to the largest diameter of a non-circular cuff body) in a range of 0.5 to 5.5 mm or in a range of 1 to 3 mm. In at least some embodiments, the cuff body 352 has a length of at least 5, 10, 20, 30, 40, or 50 mm or more. In at least some embodiments, the cuff 350 is configured to fit around a portion of the vagus, splanchnic, hapatic, hypogastric, or other nerves.

In at least some embodiments, the cuff body 352 can be formed using any suitable technique including, but not limited to, molding, casting, formed in a sheet and then shaped using adhesive as a binder, formed flat and shaped using heat, formed flat and attached to a cuff-shaped scaffold, pressed, or extruded into the cuff shape, assembled by adhering sheets together, or the like or any combination thereof. In at least some embodiments, the elongated and radial electrodes 334, 358 can be attached to the cuff body 352 using any suitable technique including, but not limited to, attaching with adhesive, molding (for example, insert molding) into the cuff body, using heat to adhere the electrodes to the cuff body, heating and pressing the electrodes into the cuff body, depositing electrode material on the cuff body, and using photolithography and etching, or the like or any combination thereof.

In at least some embodiments, once the cuff 350 has been placed in a desired position relative to the target nerve, the edges of the cuff body 352 defining the slit 360 can be sutured to capture the target nerve without undesirably compressing the target nerve. In at least some embodiments, suture holes (not shown) are optionally incorporated into the edges of the cuff 350 to allow for closing or partially closing the cuff 350 around the target nerve.

Figure 4:
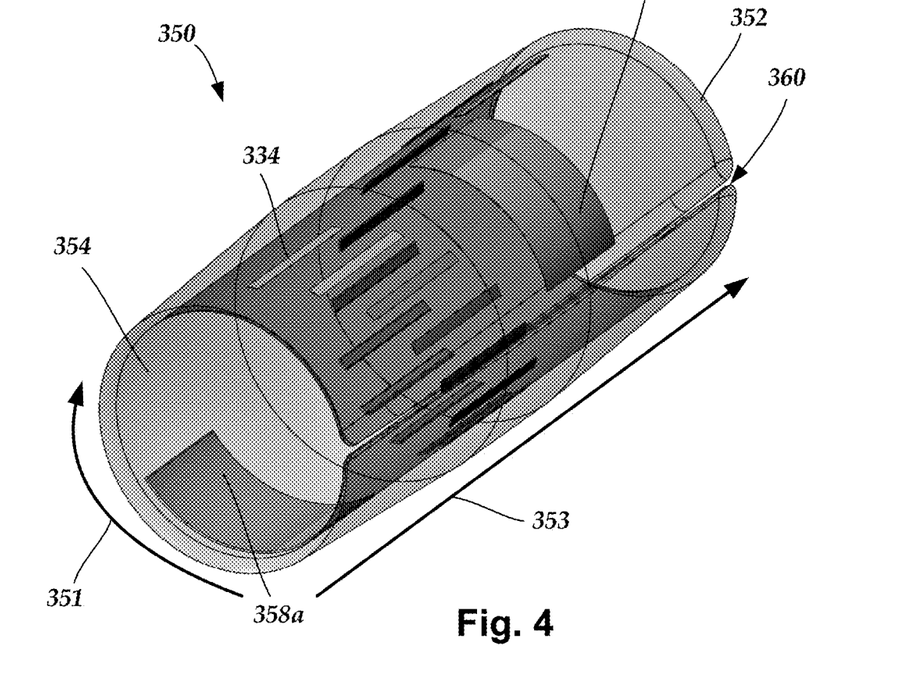
FIG. 4 is a schematic perspective view of another embodiment of a cuff with 16 helically-arranged elongated electrodes and two radial electrodes.

FIG. 4 illustrates another embodiment of a cuff 350 with a cuff body 352 and 16 longitudinally elongated electrodes 334 arranged in a single helical turn. The cuff 350 includes two radial electrodes 358a, 358b that are circumferentially offset (and, in the illustrated embodiment, circumferentially opposite) from one or more of the elongated electrodes 334.

Figure 5:
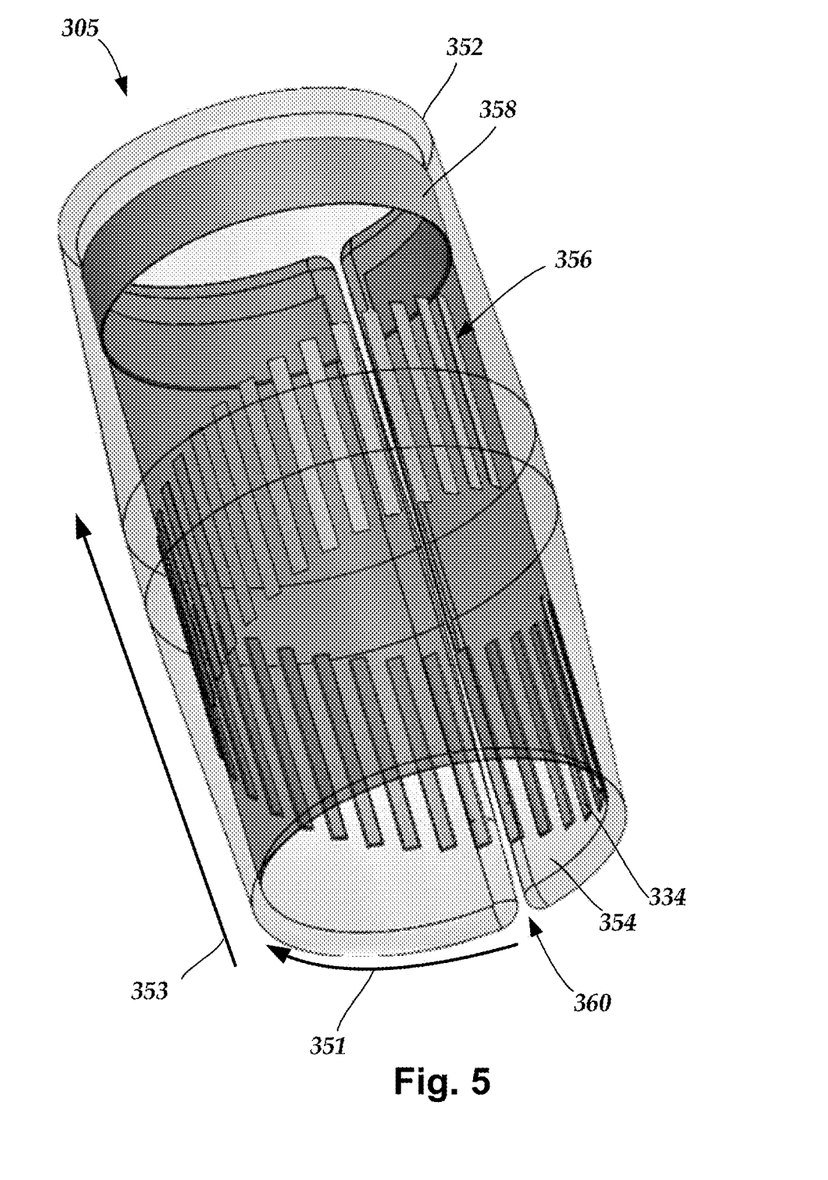
FIG. 5 is a schematic perspective view of a third embodiment of a cuff with 32 helically-arranged elongated electrodes and one radial electrode.

FIG. 5 illustrates another embodiment of a cuff 350 with a cuff body 352 and 32 longitudinally elongated electrodes 334 arranged in a single helical turn. The cuff 350 includes one radial electrode 358 at one end of the helical arrangement.

In other embodiments, radial electrodes 358 can be arranged in a set of two or more radial electrodes disposed around the circumference of the cuff body with each of the radial electrodes extending around less than half the circumference of the cuff body (for example, at least 25%, 30%, 33%, 40%, 45%, or 48% of the circumference of the cuff body). It will be understood that each set can include, for example, two, three, four, six or more radial electrodes (or any other number of radial electrodes). The radial electrodes of a set can extend a same amount around the circumference of the cuff body 352 or can extend by different amounts around the circumference of the cuff body. Each set can be identical, or the sets can have a different arrangement of radial electrodes. In at least some embodiments, the radial electrodes of a set, in combination, extend around at least 75%, 80%, 90%, or 95% of the circumference of the cuff body 352.

Figure 8:
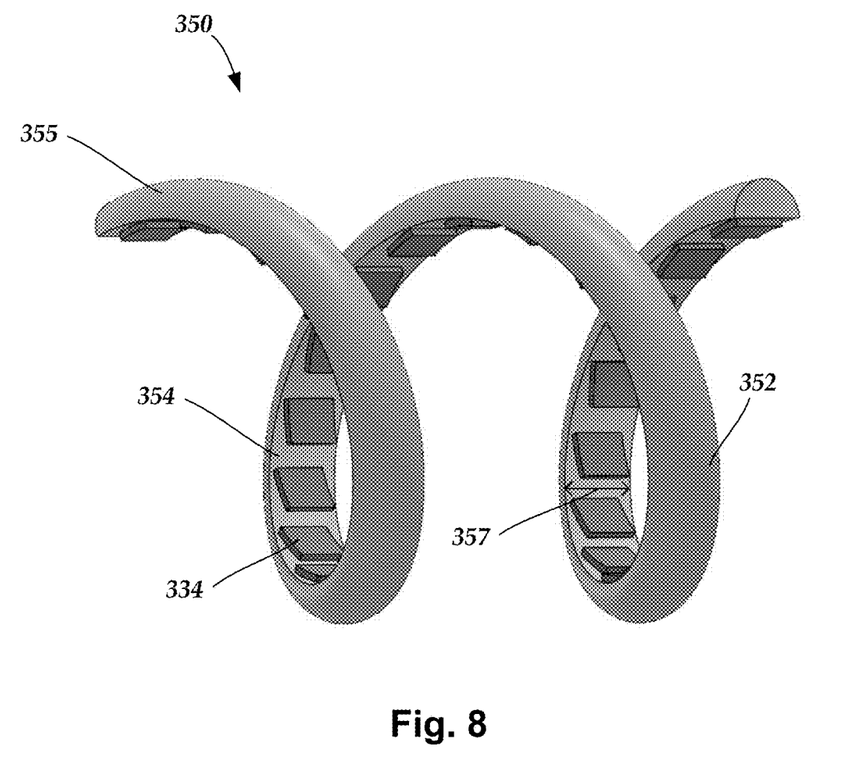
FIG. 8 is a schematic perspective view of a fourth embodiment of a cuff with a helical cuff body and electrodes arranged along the helical cuff body.

FIG. 8 illustrates yet another embodiment of a cuff 350 with a helical cuff body 352 in the form of a helix. A lead body 162 (FIG. 1) can be attached to an end of the helical cuff body 352 or the exterior surface 355 of the helical cuff body. In at least some embodiments, the helical cuff body 352 has a width 357 of at least 0.2, 0.25, 0.3, 0.4, 0.5, 0.75, or 1 mm. In at least some embodiments, the helical cuff body 352 has a width 357 of no greater than 2, 1.5, 1.25, 1, or 0.5 mm. The helical cuff body 352 can include any suitable number of full or partial helical turns helical turns including, but not limited to, 1, 1.25, 1.5, 1.75, 2, 2.5, 3, 4, 5, 6, 7, 8, 9, 10, or more helical turns. In at least some embodiments, the pitch of the helical turns of the helical cuff body 352 is no more then 1, 2, 3, 4, 5, 6, 7, 8, 9, or 10 mm. For arrangements with more than one helical turn, the helical turns can have the same or different pitches.

The electrodes 334 are arranged around the helical cuff body 352 on the interior surface 354 of the helical cuff body. Any other suitable number of electrodes can be used including, but not limited to, 8, 9, 10, 11, 12, 16, 20, 25, 28, 32, 36, 40, 48, 50, 64, 80, 99, 100, 120, 128, 150, 200, 250, 256, or more elongated electrodes in each helical turn of the helical cuff body 352. The number of electrodes 334 can be the same for each helical turn or can differ between helical turns.

In the illustrated embodiment, the electrodes 334 have a square or rectangular shape, but any other suitable shape can be used including, but not limited to, circular, oval, triangular, rhomboid, hexagonal, octagonal, irregular, or the like. In at least some embodiments, the electrodes 334 can have a width or length of at least 0.1, 0.2, 0.5, 0.6, 0.7, or 1 mm. In at least some embodiments, the electrodes 334 can have a width or length of no more than 2, 1.5, 1.25, 1, or 0.5 mm. In at least some embodiments, adjacent electrodes 334 along the helical cuff body 352 are separated by a distance of at least 0.02, 0.05, 0.07, or 0.1 mm.

Figure 6:
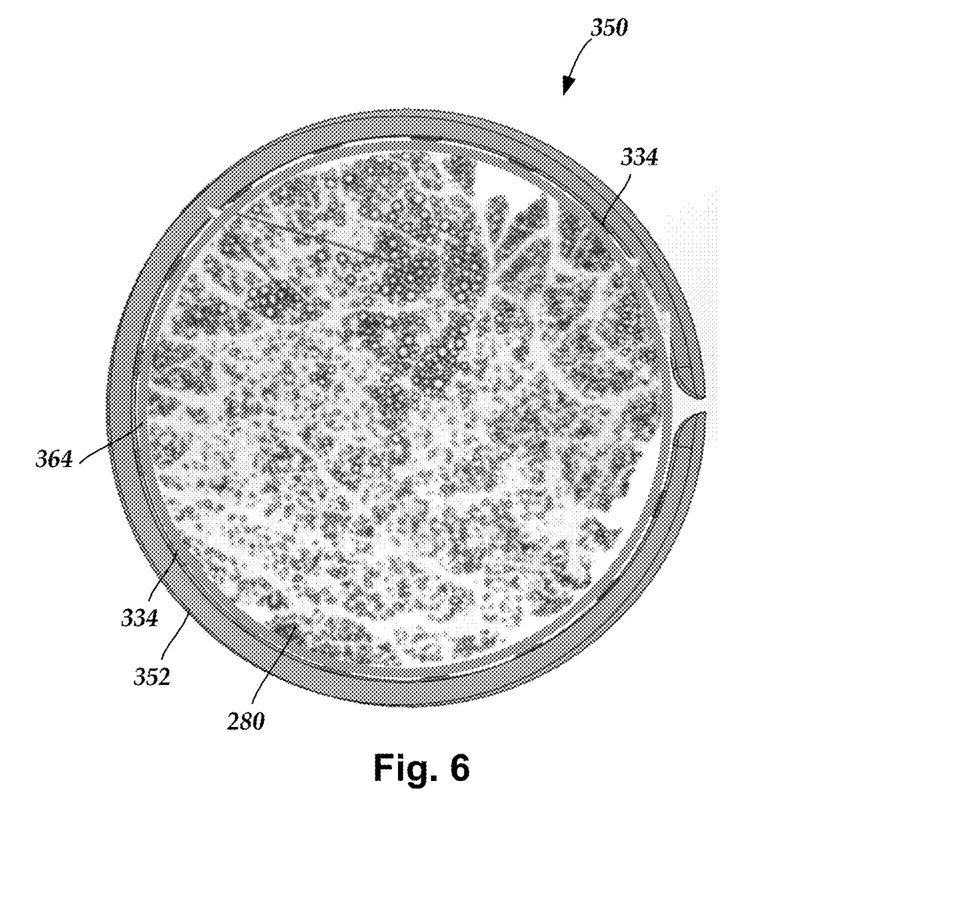
FIG. 6 is a cross-sectional view of a cuff of disposed around a portion of a nerve.

FIG. 6 illustrates a cross-section of a cuff 350 disposed around a nerve 280 with the elongated electrodes 334 arranged around the circumference of the cuff and vagus nerve. In at least some embodiments, the interior surface 354 of the cuff body 352 can be coated with a cushioning layer 364 to act as a cushion to reduce damage to the nerve. Examples of materials for the cushioning layer 364 include, but are not limited to, paraffin, a combination of isotonic saline and artificial cerebrospinal fluid, polyethylene glycol, or the like or any combination thereof. The cushioning layer 364 is made of a material that permits flow of current from the electrodes 334 to the nerve through the cushioning layer.

The cuff lead 103 (FIG. 1) can be coupled to one or more control modules 102 (FIG. 1). When the cuff lead 103 has many elongated electrodes 334, multiple control modules 102 may be used to independently control the elongated electrodes 334. Additionally or alternatively, multiplexing techniques and arrangements can be used to provide stimulation to selected elongated electrodes 334. Multiplexing arrangements may be part of the control module 102, cuff lead 103, or a separate module or the like or any combination thereof. Examples of multiplexing and of independent control and delivery of stimulation through selected electrodes can be found in U.S. Pat. Nos. 8,423,154; 8,606,362; 8,620,436; 9,308,383; 9,568,053; 10,350,413; and 10,537,741; and U.S. Patent Application Publications Nos. 2018/0071520 and 2019/0083796, all of which are incorporated herein by reference in their entireties.

Figure 7:
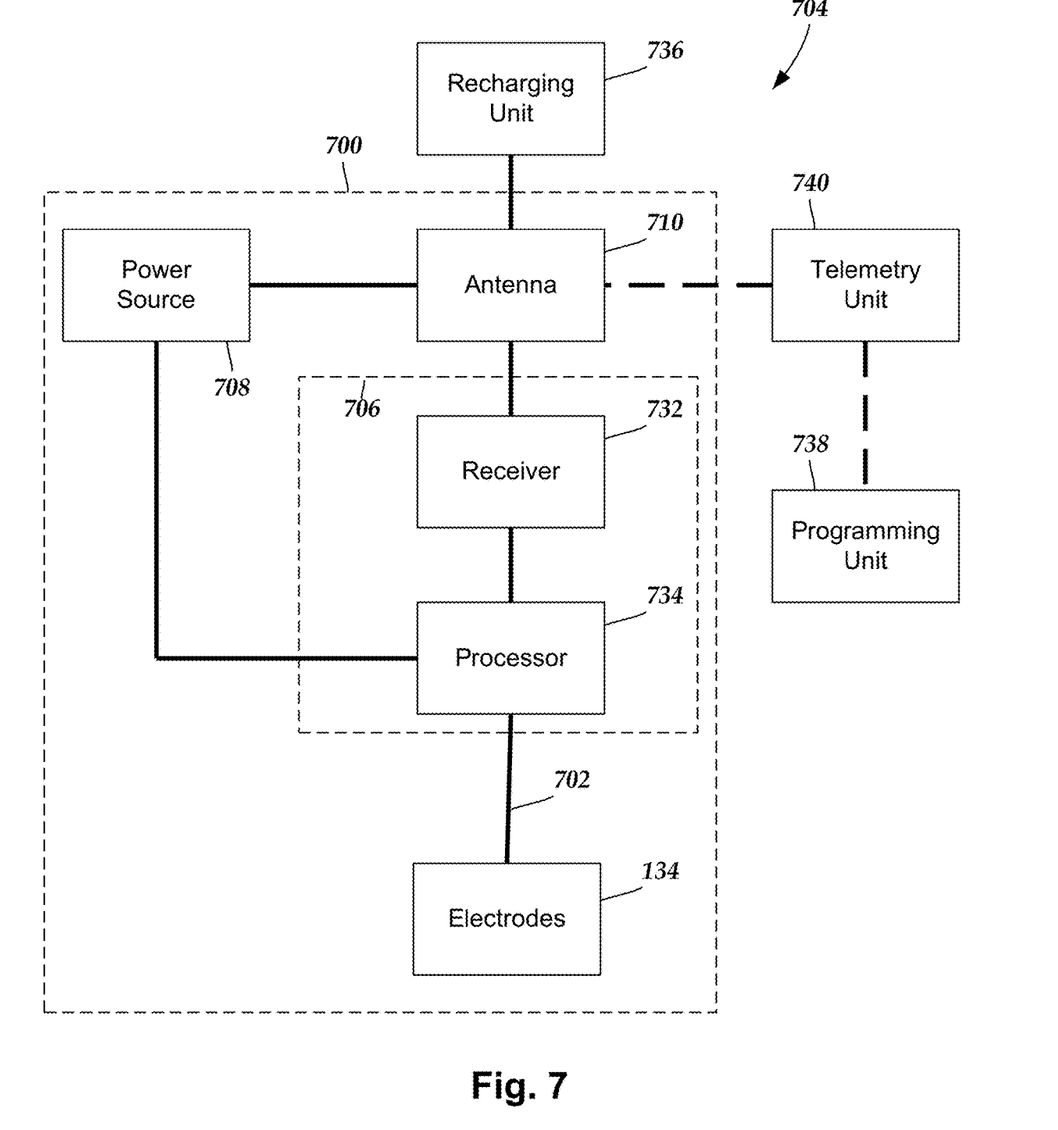
FIG. 7 is a schematic overview of one embodiment of components of an electrical stimulation arrangement.

FIG. 7 is a schematic overview of one embodiment of components of an electrical stimulation arrangement 704 that includes an electrical stimulation system 700 with a lead 702, stimulation circuitry 706, a power source 708, and an antenna 710. The electrical stimulation system can be, for example, any of the electrical stimulation systems described above. It will be understood that the electrical stimulation arrangement can include more, fewer, or different components and can have a variety of different configurations including those configurations disclosed in the stimulator references cited herein.

If the power source 708 is a rechargeable battery or chargeable capacitor, the power source may be recharged/charged using the antenna 710, if desired. Power can be provided for recharging/charging by inductively coupling the power source 708 through the antenna 710 to a recharging unit 736 external to the user. Examples of such arrangements can be found in the references identified above.

In at least some embodiments, electrical current is emitted by the electrodes (such as electrodes 134 in FIG. 1) on the lead 702 to stimulate nerve fibers, muscle fibers, or other body tissues near the electrical stimulation system. The stimulation circuitry 706 can include, among other components, a processor 734 and a receiver 732. The processor 734 is generally included to control the timing and electrical characteristics of the electrical stimulation system. For example, the processor 734 can, if desired, control one or more of the timing, frequency, strength, duration, and waveform of the pulses. In addition, the processor 734 can select which electrodes can be used to provide stimulation, if desired. In some embodiments, the processor 734 selects which electrode(s) are cathodes and which electrode(s) are anodes. In some embodiments, the processor 734 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 738 that, for example, allows modification of pulse characteristics. In the illustrated embodiment, the processor 734 is coupled to a receiver 732 which, in turn, is coupled to the antenna 710. This allows the processor 734 to receive instructions from an external source to, for example, direct the pulse characteristics and the selection of electrodes, if desired.

In at least some embodiments, the antenna 710 is capable of receiving signals (e.g., RF signals) from an external telemetry unit 740 that is programmed by the programming unit 738. The programming unit 738 can be external to, or part of, the telemetry unit 740. The telemetry unit 740 can be a device that is worn on the skin of the user or can be carried by the user and can have a form similar to a pager, cellular phone, or remote control, if desired. As another alternative, the telemetry unit 740 may not be worn or carried by the user but may only be available at a home station or at a clinician's office. The programming unit 738 can be any unit that can provide information to the telemetry unit 740 for transmission to the electrical stimulation system 700. The programming unit 738 can be part of the telemetry unit 740 or can provide signals or information to the telemetry unit 740 via a wireless or wired connection. One example of a suitable programming unit is a computer operated by the user or clinician to send signals to the telemetry unit 740.

The signals sent to the processor 734 via the antenna 710 and the receiver 732 can be used to modify or otherwise direct the operation of the electrical stimulation system 700. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery.

Optionally, the electrical stimulation system 700 may include a transmitter (not shown) coupled to the processor 734 and the antenna 710 for transmitting signals back to the telemetry unit 740 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 734 may also be capable of transmitting information about the pulse characteristics so that a user or clinician can determine or verify the characteristics.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected is:

1. An electrical stimulation lead comprising:
    a cuff comprising
        a cuff body having an exterior surface, an interior surface, and a circumference,
        a plurality of longitudinally elongated electrodes disposed on the interior surface of the cuff body and helically arranged with each of the longitudinally elongated electrodes longitudinally offset relative to any adjacent longitudinally elongated electrodes, wherein, for all of the longitudinally elongated electrodes, immediately adjacent ones of the longitudinally elongated electrodes longitudinally overlap with each other and have a longitudinal offset of proximal ends of the longitudinally elongated electrodes no more than 75% of a length of the longitudinally elongated electrodes, wherein each of the longitudinally elongated electrodes has a width of no more than 100 μm and a length of at least 0.5 mm, and
        a longitudinal slit extending through the cuff body and further extending along an entire length of the cuff body, the longitudinal slit operable to receive a portion of a target nerve from a region outside of the cuff to within the cuff body;
    a lead body coupled to the cuff; and
    a plurality of conductors extending through the lead body and the cuff with the conductors electrically coupled to the longitudinally elongated electrodes.

2. The electrical stimulation lead of claim 1, wherein the longitudinally elongated electrodes are arranged in at least one helical turn.

3. The electrical stimulation lead of claim 2, wherein each of the at least one helical turn includes at least eight of the longitudinally elongated electrodes.

4. The electrical stimulation lead of claim 3, wherein each of the at least one helical turn of the cuff body has a pitch of at least 1 mm.

5. The electrical stimulation lead of claim 3, wherein adjacent pairs of the longitudinally elongated electrodes are separated by at least 0.02 mm.

6. The electrical stimulation lead of claim 1, wherein the longitudinally elongated electrodes are arranged in at least two helical turns.

7. The electrical stimulation lead of claim 6, wherein each of the helical turns includes at least eight of the longitudinally elongated electrodes.

8. The electrical stimulation lead of claim 6, wherein the longitudinally elongated electrodes of each of the helical turns are longitudinally aligned with corresponding ones of the longitudinally elongated electrodes of each of the other helical turns.

9. The electrical stimulation lead of claim 6, wherein the longitudinally elongated electrodes of at least one of the helical turns are circumferentially staggered relative to corresponding ones of the longitudinally elongated electrodes of at least one of the other helical turns.

10. The electrical stimulation lead of claim 1, wherein the plurality of longitudinally elongated electrodes comprises at least 20 of the longitudinally elongated electrodes.

11. The electrical stimulation lead of claim 1, wherein each of the longitudinally elongated electrodes is longitudinally offset from each adjacent one of the longitudinally elongated electrodes by at least 0.2 mm or by at least 10 percent of the length of the longitudinally elongated electrodes.

12. The electrical stimulation lead of claim 1, wherein the cuff further comprises at least one radial electrode extending around at least 40% of the circumference of the cuff body.

13. The electrical stimulation lead of claim 12, wherein at least one of the at least one radial electrode is disposed on the cuff body at an end of the helical arrangement of the longitudinally elongated electrodes or the at least one radial electrodes comprises two radial electrode disposed at opposite ends of the helical arrangement of the longitudinally elongated electrodes.

14. The electrical stimulation lead of claim 1, further comprising a cushioning layer disposed over the interior surface of the cuff body.

15. The electrical stimulation lead of claim 1, wherein the cuff body has a length of at least 10 mm.

16. The electrical stimulation lead of claim 1, further comprising a plurality of terminals disposed along the lead body and electrically coupled to the longitudinally elongated electrodes by the conductors.

17. An electrical stimulation system, comprising:
    the electrical stimulation lead of claim 1; and
    a control module configured to receive a portion of the lead body of the electrical stimulation lead and to electrically couple to the longitudinally elongated electrodes.

18. The electrical stimulation lead of claim 1, wherein each of the longitudinally elongated electrodes has a length of at least 2 mm.

19. The electrical stimulation lead of claim 1, wherein, for all of the longitudinally elongated electrodes, a longitudinal offset between the proximal ends of immediately adjacent ones of the longitudinally elongated electrodes is no more than 30% of a length of the longitudinally elongated electrodes.

20. The electrical stimulation lead of claim 1, wherein each of the longitudinally elongated electrodes has an aspect ratio (length/width) of at least 10.

* * * * *